US008087313B2

(12) United States Patent  (10) Patent No.: US 8,087,313 B2
Walker  (45) Date of Patent: Jan. 3, 2012

(54) METHOD FOR DETERMINING EXPECTED WATER UPTAKE IN HYGROSCOPIC MATERIAL

(75) Inventor: Eric Walker, Dublin, OH (US)

(73) Assignee: Honda Motor Co., Ltd., Tokyo (JP)

(*) Notice: Subject to any disclaimer, the term of this patent is extended or adjusted under 35 U.S.C. 154(b) by 497 days.

(21) Appl. No.: 12/420,245

(22) Filed: Apr. 8, 2009

(65) Prior Publication Data

US 2010/0257918 A1  Oct. 14, 2010

(51) Int. Cl.
  *G01N 33/00* (2006.01)
(52) U.S. Cl. ............................................. 73/866
(58) Field of Classification Search .................. 73/866
  See application file for complete search history.

(56) References Cited

U.S. PATENT DOCUMENTS

| | | | |
|---|---|---|---|
| 3,987,218 A | 10/1976 | Haschke et al. | |
| 4,779,468 A | 10/1988 | Susuki | |
| 4,823,595 A | 4/1989 | Hamed et al. | |
| 5,685,192 A * | 11/1997 | Shriner et al. | 73/73 |
| 6,659,638 B1 | 12/2003 | Hardcastel | |
| 6,998,455 B1 | 2/2006 | Ohta et al. | |
| 7,100,428 B1 * | 9/2006 | Dziki | 73/73 |
| 7,310,995 B2 * | 12/2007 | Dziki | 73/73 |
| 7,661,296 B2 * | 2/2010 | Dziki | 73/73 |
| 2006/0260385 A1 | 11/2006 | Galun et al. | |
| 2007/0107500 A1 | 5/2007 | Patel | |

OTHER PUBLICATIONS

Translation of DIN 75 220 Nov. 1992.

* cited by examiner

*Primary Examiner* — Hezron E Williams
*Assistant Examiner* — Rodney T Frank
(74) *Attorney, Agent, or Firm* — Mark E. Duell, Esq.; Emerson Thomson Bennett

(57) ABSTRACT

Some embodiments relate to methods and processes for determining how a range of weather conditions can affect a selected physical parameter of a material. In some embodiments the weather conditions can include relative humidity and/or temperature, and the selected physical parameter can be mass and or dimensions. For instance, some embodiments can be used to estimate the amount of water that a material may be expected to absorb under in-service conditions. In some embodiments the amount of water can defined by a range bounded by amounts observed at opposing extremes of simulated conditions.

18 Claims, 1 Drawing Sheet

METHOD FOR DETERMINING EXPECTED WATER UPTAKE IN HYGROSCOPIC MATERIAL

I. BACKGROUND OF THE INVENTION

A. Field of Invention

Figure 1:
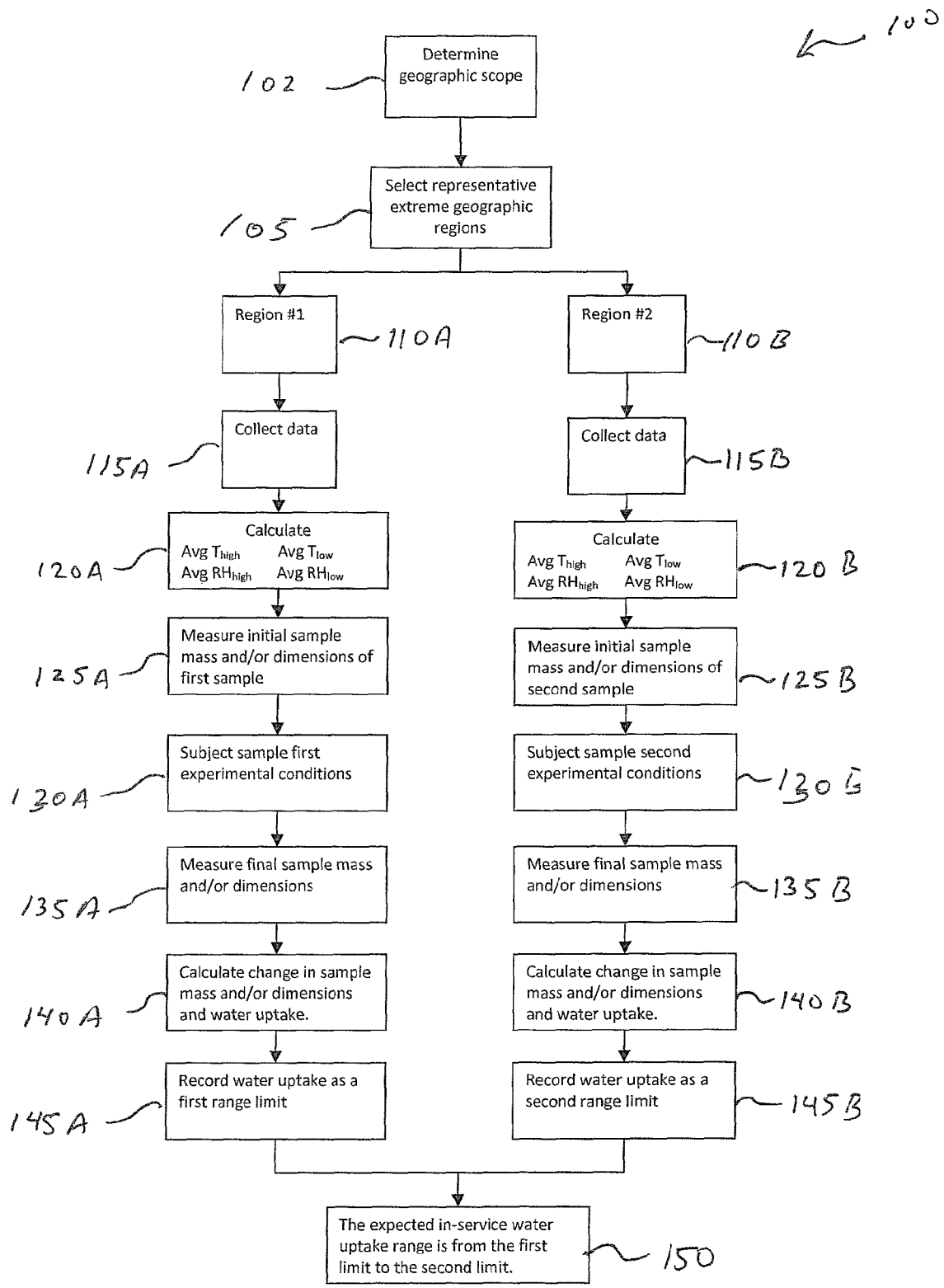

This invention generally relates to methods for determining water uptake of a material under predicted in-service conditions.

B. Description of the Related Art

Materials are known to be affected by, and may change according to, in-service environmental conditions. Materials that are used in outdoor applications and subjected to extreme weather can be particularly susceptible to environmental effects. Thus, it is known to test materials using simulated weathering conditions. A wide variety of weathering chambers and devices have been developed for this purpose. Some materials may be used in vehicles such as automobiles, boats, aircraft or the like, and thus may experience a wide variety of weather conditions that may promote water up-take to varying degrees. Since water up-take can cause changes in physical dimensions, mass, material strength and other properties it is desirable to have a method to predict the amount of water that a material is likely to absorb while in service.

The some embodiments provide methods for predicting water uptake in a wide variety of materials.

II. SUMMARY OF THE INVENTION

Some embodiments relate to a method for estimating in-service water uptake range in hygroscopic polymeric materials comprising the steps of selecting a plurality of geographic regions that are representative of in-service temperature and relative humidity extremes to which a hygroscopic polymeric material is expected to be subjected; obtaining temperature and relative humidity data in the selected plurality of geographic regions over a predetermined period of time and at a predetermined interval; providing a first test sample and a second test sample of the hygroscopic polymeric material; determining a change in mass, of the first test sample after subjecting the first test sample to a simulated day period and a simulated night period representative of a first selected geographic location, and converting the change in mass to an amount of water taken up by the first test sample; recording the water uptake of the first test sample as a first range limit; determining a change in mass of the second test sample after subjecting the second test sample to a simulated day period and a simulated night period representative of a second selected geographic location, and converting the change in mass to an amount of water taken up by the second test sample; recording the water uptake of the second test sample as a second range limit; and determining the estimated water uptake range to be the range defined by the first and second range limits.

Other embodiments can comprise a method for estimating in-service water uptake range in materials comprising the steps of: identifying the geographic scope of a material's expected use; selecting two geographic regions that are representative of opposing in-service relative humidity extremes to which the material is expected to be subjected; obtaining temperature and relative humidity data in the two selected geographic regions over a predetermined period of time and at a predetermined interval; calculating average relative humidity, and average temperature for the two selected geographic regions; providing at least a first test sample and a second test sample of the material; simulating a first set of extreme in-service weather conditions and an opposing second set of extreme in-service weather conditions using the calculated temperature and relative humidity quantities, and subjecting each test sample to one set of conditions; determining a change in mass, of the first test sample and the second test sample after subjecting the test samples to respective sets of simulated extreme in-service weather conditions, wherein the step of determining the change in mass of the first and second test samples further comprises measuring the initial mass of the test sample at a selected reference temperature and relative humidity; subjecting the test sample to a simulated day period comprising an average high temperature and average low relative humidity; subjecting the test sample to a simulated night period, comprising an average low temperature and average high relative humidity, wherein the simulated day and night periods are substantially contiguous; and measuring the final mass; converting the mass changes into amounts of water taken up; recording the water uptake of the first test sample as a first range limit, and the water uptake of the second test sample as an opposing second range limit; and determining the estimated water uptake range to be the range defined by the first and second range limits.

Other benefits and advantages will become apparent to those skilled in the art to which it pertains upon reading and understanding of the following detailed specification.

III. BRIEF DESCRIPTION OF THE DRAWINGS

The invention may take physical form in certain parts and arrangement of parts, embodiments of which will be described in detail in this specification and illustrated in the accompanying drawings which form a part hereof and wherein:

FIG. 1 is a flowchart showing a process embodiment according to the present invention.

IV. DETAILED DESCRIPTION OF THE INVENTION

Some embodiments comprise a process for estimating the amount of in-service water uptake by a material that is used at least partially outdoors. The subject material can have any degree of hygroscopic character. For instance, very hygroscopic materials can be assessed as well as materials with very little hygroscopic character. Even materials that are substantially hydrophobic can be assessed according to some embodiments.

An embodiment can include identifying the geographic scope of a material's service. A plurality of representative geographic regions can be selected from the identified scope. The selected regions can represent the extremes of expected weather conditions to which the material is likely to be subjected in-service. Weather data can be collected for each representative region over a predetermined time and at a predetermined interval. The data can be used to calculate quantities that can be used to simulate extreme in-service weather conditions. Material samples are then subjected to simulated in-service weather conditions that represent the extreme ends of expected conditions, and a change in a physical parameter, such as mass and/or dimensions, is recorded.

Observed weather data can be used to calculate such quantities as average temperatures and average relative humidities of each representative geographic region. More specifically, in some embodiments the calculated quantities can include average high temperature, average low temperature, average high humidity, and average low humidity. Still further, the quantities can be constrained to data collected a selected times of the year and/or day. For instance, in some embodiments average high temperatures can be calculated from data collected during a summer day period, and average low temperatures can be calculated for data collected during a summer night period. Similar calculations can be done for relative humidity or other relevant parameters.

Some relevant physical parameters can include one or more of: day, night, month, season, year, temperature, high temperature, low temperature, average temperature, average high or low temperature, relative humidity, high relative humidity, low relative humidity, average relative humidity, average high or low relative humidity, data sampling time interval and the like or any combination thereof. Other parameters that can be relevant to some materials can include irradiance, the frequency spectrum of incident radiation, power spectrum of incident radiation, or atmospheric composition (e.g. oxygen content, oxidant content, inert content, caustic vapor content, organic vapor content, and the like).

According to some embodiments a plurality of samples of a material can be provided for determining water uptake of the material. Reference data can be collected for a sample prior to subjecting it to experimental conditions. For instance, the initial mass and/or dimensions of the sample can be measured. The sample can then be subjected to experimental conditions mimicking a first set of expected in-service extreme conditions. Following the experimental treatment, the sample's final mass and/or dimensions can be measured, and the change in mass and/or dimensions can be recorded. The result can then be related to a quantity of water taken up by the material. The initial mass and/or dimensions of a second sample can be measured and the second sample can then be subjected to a second set of experimental conditions representing an opposing extreme of expected in-service conditions. Following experimental treatment, the final mass and/or dimensions of the second sample can be measured, and the change in mass and/or dimensions can be recorded. The second result can then be related to a quantity of water taken up by the material.

The amount of water taken up by the material under opposing extremes of temperature and/or humidity can be used to define a range of expected water uptake. For example, if the material takes up n grams of water under a first set of extreme conditions and 0.5 n grams of water under an opposing set of extreme conditions then the range of expected water uptake for the material is from 0.5 n to n grams.

In some embodiments only two sets of opposing extreme conditions are chosen. However, in other embodiments additional sets of conditions may be necessary, for instance, in some multivariate experiments. Assuming a case where only two opposing extreme conditions sets are necessary, the opposing sets can be selected as follows. First the geographic scope of the material's use is identified. For example, it may be known that the material is to be used in a product sold only in the United States. Thus, the geographic scope can be identified as the United States. Then, two locations representing the opposing extremes of environmental conditions are chosen from within the identified geographic scope. For instance, if the United States is identified as the geographic scope of use, then the extremes of relative humidity conditions could be represented by Phoenix Ariz., and Miami Fla. Next, relative humidity and temperature data can be collected from the locations over a predetermined period such as a day, a week, a month, a year, or a plurality of years. Furthermore, data may be sampled at a predetermined interval such as a second, a minute, an hour, a plurality of hours, or a day. These data can then be used to calculate parameters for laboratory simulations of weather conditions.

Referring now to the drawings wherein the showings are for purposes of illustrating embodiments of the invention only and not for purposes of limiting the same, FIG. 1 is a flowchart showing a process 100 according to an embodiment. The process begins by first determining the geographic scope 102 of a material's use. Then representative extreme geographic regions 110A, 110B are selected 105, that can represent for instance the extremes of humidity and/or temperature to which the material is subjected in-service. Data is then collected for region one 115A and for region two 115B. The data are processed and used to calculate physical quantities for creating a simulation 120A, 120B. In this embodiment average high and low temperatures, and average high and low relative humidities are calculated. The mass and/or dimensions of a first sample 125A and a second sample 125B are measured. The first and second samples are then subjected to opposing extremes of simulated weather conditions 130A, 130B wherein the simulation is created using the quantities calculated in steps 120A and 120B. Following the experimental treatment the masses and/or dimensions of the samples are measured again 135A, 135B. The mass and/or dimensional change between steps 125A, 125B and 135A, 135B is calculated and the differences are used to calculate the amount of water taken up by the respective samples under opposing condition extremes 140A, 140B. For instance, one of skill in the art will recognize that a mass change can be converted into the number (e.g. in moles) of water molecules absorbed by the material. The amounts of water uptake are thus recorded 145A, 145B. Accordingly, the range of expected water uptake for the material is determined 150 to be a range bounded by the water uptake calculated in steps 145A and 145B.

The embodiments have been described, hereinabove. It will be apparent to those skilled in the art that the above methods and apparatuses may incorporate changes and modifications without departing from the general scope of this invention. It is intended to include all such modifications and alterations insofar as they come within the scope of the appended claims or the equivalents thereof.

I claim:

1. A method for estimating in-service water uptake range in materials comprising the steps of:
   identifying the geographic scope of a material's expected use;
   selecting two geographic regions that are representative of opposing in-service relative humidity extremes to which the material is expected to be subjected;
   obtaining temperature and relative humidity data in the two selected geographic regions over a predetermined period of time and at a predetermined interval;
   calculating average relative humidity, and average temperature for the two selected geographic regions;
   providing at least a first test sample and a second test sample of the material;
   simulating a first set of extreme in-service weather conditions and an opposing second set of extreme in-service weather conditions using the calculated temperature and relative humidity quantities, and subjecting each test sample to one set of conditions;
   determining a change in mass, of the first test sample and the second test sample after subjecting the test samples to respective sets of simulated extreme in-service weather conditions;
   converting the mass changes into amounts of water taken up;

recording the water uptake of the first test sample as a first range limit, and the water uptake of the second test sample as an opposing second range limit; and determining the estimated water uptake range to be the range defined by the first and second range limits.

2. The process of claim 1, wherein the predetermined data sampling period for the step of obtaining temperature and relative humidity data encompasses one year.

3. The process of claim 1, wherein the predetermined data sampling interval for the step of obtaining temperature and relative humidity data is from about one second to about one day.

4. The process of claim 1, wherein the step of calculating average temperature comprises calculating an average high temperature and an average low temperature.

5. The process of claim 1, wherein the step of calculating an average relative humidity comprises calculating an average high humidity and an average low humidity.

6. The process of claim 1, wherein the step of determining the change in mass of the first and second test samples further comprises:
- measuring the initial mass of the test sample at a selected reference temperature and relative humidity, and/or measuring the length of a major axis at a reference temperature and relative humidity;
- subjecting the test sample to a simulated day period comprising an average high temperature and average low relative humidity;
- subjecting the test sample to a simulated night period, comprising an average low temperature and average high relative humidity, wherein the simulated day and night periods are substantially contiguous; and
- measuring the final mass, and/or the final length of the major axis.

7. The process of claim 6, wherein the step of measuring the initial mass comprises taking the measurement at about 25 degrees Celsius, and less than 50 percent relative humidity.

8. The process of claim 6, wherein the step of subjecting the test sample to a set of conditions comprises a simulated day period further comprising an average high temperature and an average low relative humidity of the first or second geographic location for a predetermined length of time.

9. The process of claim 6, wherein the step of subjecting the test sample to a set of conditions comprises a simulated night period further comprising an average low temperature and an average high relative humidity of the first or second geographic location for a predetermined length of time.

10. A method for estimating in-service water uptake range in materials comprising the steps of:
- identifying the geographic scope of a material's expected use;
- selecting two geographic regions that are representative of opposing in-service relative humidity extremes to which the material is expected to be subjected;
- obtaining temperature and relative humidity data in the two selected geographic regions over a predetermined period of time and at a predetermined interval;
- calculating average relative humidity, and average temperature for the two selected geographic regions;
- providing at least a first test sample and a second test sample of the material;
- simulating a first set of extreme in-service weather conditions and an opposing second set of extreme in-service weather conditions using the calculated temperature and relative humidity quantities, and subjecting each test sample to one set of conditions;
- determining a change in mass, of the first test sample and the second test sample after subjecting the test samples to respective sets of simulated extreme in-service weather conditions, wherein the step of determining the change in mass of the first and second test samples further comprises measuring the initial mass of the test sample at a selected reference temperature and relative humidity; subjecting the test sample to a simulated day period comprising an average high temperature and average low relative humidity; subjecting the test sample to a simulated night period, comprising an average low temperature and average high relative humidity, wherein the simulated day and night periods are substantially contiguous; and measuring the final mass;
- converting the mass changes into amounts of water taken up;
- recording the water uptake of the first test sample as a first range limit, and the water uptake of the second test sample as an opposing second range limit; and
- determining the estimated water uptake range to be the range defined by the first and second range limits.

11. The process of claim 10, wherein the predetermined data sampling period for the step of obtaining temperature and relative humidity data encompasses one year.

12. The process of claim 10, wherein the predetermined data sampling interval for the step of obtaining temperature and relative humidity data is from about one second to about one day.

13. The process of claim 10, wherein the step of calculating average temperature comprises calculating an average high temperature and an average low temperature.

14. The process of claim 10, wherein the step of calculating an average relative humidity comprises calculating an average high humidity and an average low humidity.

15. The process of claim 10, wherein the step of measuring the initial mass comprises taking the measurement at about 25 degrees Celsius, and less than 50 percent relative humidity.

16. The process of claim 10, wherein the step of subjecting the test sample to a set of conditions comprises a simulated day period further comprising an average high temperature and an average low relative humidity of the first or second geographic location for a predetermined length of time.

17. The process of claim 10, wherein the step of subjecting the test sample to a set of conditions comprises a simulated night period further comprising an average low temperature and an average high relative humidity of the first or second geographic location for a predetermined length of time.

18. A method for estimating in-service water uptake range in materials comprising the steps of:
- identifying the geographic scope of a material's expected use;
- selecting two geographic regions that are representative of opposing in-service relative humidity extremes to which the material is expected to be subjected;
- obtaining temperature and relative humidity data in the two selected geographic regions over a period of time up to about one year, and at a sampling interval from about one second to about one day;
- calculating an average high relative humidity, an average low relative humidity, an average high temperature and an average low temperature for the two selected geographic regions;
- providing at least a first test sample and a second test sample of the material;
- simulating a first set of extreme in-service weather conditions and an opposing second set of extreme in-service weather conditions using the calculated temperature and relative humidity quantities, and subjecting each test sample to one set of conditions, wherein the first and second sets of conditions each comprise a simulated day period and a substantially contiguous simulated night period;

determining a change in mass, of the first test sample and the second test sample after subjecting the test samples to respective sets of simulated extreme in-service weather conditions, wherein the step of determining the change in mass of the first and second test samples further comprises measuring the initial mass of the test sample at about 25 degrees Celsius and less than about 50 percent relative humidity; subjecting the test sample to a simulated day period comprising an average high temperature and average low relative humidity; subjecting the test sample to a simulated night period, comprising an average low temperature and average high relative humidity, wherein the simulated day and night periods are substantially contiguous; and measuring the final mass;

converting the mass changes into amounts of water taken up;

recording the water uptake of the first test sample as a first range limit, and the water uptake of the second test sample as an opposing second range limit; and determining the estimated water uptake range to be the range defined by the first and second range limits.

* * * * *